US008697636B2

(12) United States Patent
Crost et al.

(10) Patent No.: US 8,697,636 B2
(45) Date of Patent: Apr. 15, 2014

(54) RUMC PEPTIDES WITH ANTIMICROBIAL ACTIVITY

(75) Inventors: Emmanuelle Crost, Marseilles (FR); Michel Fons, Aix en Provence (FR); Pierre-Andre Geraert, Rochecorbon (FR)

(73) Assignee: Adisseo France S.A.S. (FR)

( * ) Notice: Subject to any disclaimer, the term of this patent is extended or adjusted under 35 U.S.C. 154(b) by 917 days.

(21) Appl. No.: 12/601,828

(22) PCT Filed: May 16, 2008

(86) PCT No.: PCT/FR2008/000683

§ 371 (c)(1), (2), (4) Date: May 12, 2010

(87) PCT Pub. No.: WO2008/152252

PCT Pub. Date: Dec. 18, 2008

(65) Prior Publication Data

US 2012/0263688 A1 Oct. 18, 2012

(30) Foreign Application Priority Data

May 29, 2007 (FR) ..................................... 07 03789

(51) Int. Cl.

| | |
|---|---|
| ***A61K 38/00*** | (2006.01) |
| ***C12P 21/06*** | (2006.01) |
| ***C12P 21/04*** | (2006.01) |
| ***C12N 1/20*** | (2006.01) |
| ***C07H 21/02*** | (2006.01) |
| ***C12N 15/00*** | (2006.01) |
| ***C12N 1/12*** | (2006.01) |

(52) U.S. Cl.

USPC ......... 514/2.4; 435/69.1; 435/71.1; 435/93.4; 435/252.1; 435/252.2; 435/320.1; 530/300; 536/23.1

(58) Field of Classification Search

None

See application file for complete search history.

(56) References Cited

FOREIGN PATENT DOCUMENTS

WO WO 94/15961 * 7/1994

OTHER PUBLICATIONS

Conversion Factors, Units and Abbreviations. Invitrogen. http://www.invitrogen.com/etc/medialib/en/filelibrary/pdf.Par.7634.File.dat/Conversion_Factors_Y14479_Conversion.pdf obtained Jan. 9, 2013.*

Invitrogen Catalog, 1997 (primers for first strand cDNA synthesis under CDNA Synthesis and Libraries section).*

Crost et al. Biochimie 93 (2011) 1487-1494.*

International Search Report PCT/FR2008/000683; Dated Dec. 5, 2008.

J.Debard, "Ruminococcin A, a New Lantibiotic Produced by a *Ruminococcus gnavus* Strain Isolated from Human Feces" Applied and Environmental Microbiology , Sep. 2001, vol. 67, No. 9, pp. 4111-4118.

Ana Gomez, et al., Trypsin Mediates Growth Phase-Dependent Transcriptional Regulation of Genes Involved in Biosynthesis of Ruminococcin A, a Lantibiotic Produced by a *Ruminococcus gnavus* Strain from a Human Intestinal Microbiota, Journal of Bacteriology, Jan. 2002, vol. 184, No. 1, pp. 18-28.

* cited by examiner

*Primary Examiner* — Oluwatosin Ogunbiyi

(74) *Attorney, Agent, or Firm* — Cantor Colburn LLP

(57) ABSTRACT

The present invention relates to the RumC1, RumC2 and RumC3 peptides with antimicrobial activity, and also to the genes encoding these peptides and isolated from *Ruminococcus gnavus* E1.

18 Claims, 9 Drawing Sheets

RUMC PEPTIDES WITH ANTIMICROBIAL ACTIVITY

The invention relates to the peptides RumC1, RumC2 and RumC3 with antimicrobial activity, and also to the genes coding for these peptides and isolated from *Ruminococcus gnavus* E1.

Certain bacterial strains have the capacity to release substances with a bacteriostatic or bactericidal effect on their competitors. These antimicrobial substances may be of organic nature, for example organic acids or hydrogen peroxide (Ross et al., Int. J. Food Microbiol. 79, 3-16, 2002), or of peptide nature. Enzymatically synthesized antimicrobial peptides that form the class of antibiotics (Mootz et al., Curr. Opin. Chem. Biol. 1, 543-551, 1997; Keating et al., Curr. Opin. Chem. Biol. 3, 598-606, 1999), and ribosomally produced peptides that form the class of bacteriocins (Jacob et al., Ann. Inst. Pasteur (Paris) 84, 222-224, 1953) are also distinguished.

Bacteriocins are arousing increasing interest in the world of research and industry; they might provide alternative solutions to the use of antibiotics, especially in rearing (Luchansky, Antonie Van Leeuwenhoek 76, 335, 1999; O'Sullivan et al., Biochimie 84, 593-604, 2002).

Many heterologous expression systems of these bacteriocins have been developed in recent years. In particular, Morriset et al. (Morisset et al., Appl. Environ. Microbiol., 70, 4672-4680, 2004) have expressed variants of mesentricin Y105, a class IIa bacteriocin produced by *Leuconostoc mesenteroides* subsp. *mesenteroides* Y105, in *Leuconostoc mesenteroides* subsp. *dextranicum* DSM20484. Similarly, Flynn et al. (Microbiol., 148, 973-984, 2002) achieved the expression of ABP-118, a class IIb bacteriocin originally produced by *Lactobacillus salivarius* subsp. *salivarius* UCC118, in the hosts *Lactobacillus plantarum, Lactococcus lactis* and *Bacillus cereus.*

In addition, several tests have been conducted to express bacteriocins in the bacterium *Escherichia coli* (McCormick et al., Appl. Environ. Microbiol., 64, 4757-4766, 1998; Garneau et al., Appl. Environ. Microbiol., 69, 1352-1358, 2003; Biet et al., Microbiol., 144, 2845-2854, 1998; Miller et al., Appl. Environ. Microbiol., 64, 14-20, 1998; Richard et al., J. Bacteriol., 186, 4276-4284, 2004; Kloche et al., Appl. Microbiol. Biotechnol., 67:532-538, 2005), the yeast *Saccharomyces cerevisiae* (Schoeman et al., Yeast, 15, 647-656, 1999; Van Reenen et al., Int. J. Food Microbiol., 81, 29-40, 2003) and in lactic acid bacteria (Rodriguez et al., Int. J. Food Microbiol., 80, 101-116, 2003).

Many studies have thus been performed for the purpose of identifying novel bacteriocins and for producing these bacteriocins.

The digestive ecosystem is formed of an abundant and very complex microflora combining bacteria, yeasts and Archeae. This microbiota is essentially anaerobic, and bacteria of the genera *Bacteroides, Eubacterium, Clostridium, Ruminococcus, Bifidobacterium* and *Fusobacterium* are mainly found (Suau et al., Appl. Environ. Microbiol. 65, 4799-4807, 1999). The microflora has a major impact on the health of the host. It is especially involved in the toxification and detoxication of metabolic compounds derived from food (Hughes and Rowland Microbial Ecology Health Disease 2, 179-185, 2000). It is also capable of modulating the expression of enterocytic functions (Bry et al., Science 273, 1380-1383, 1996; Hooper et al., Science 291, 881-884, 2001). Finally, it plays a fundamental role in protecting the host against invasion by potentially pathogenic exogenous bacteria (Ducluzeau et al., Microbial Ecology and Intestinal Infections, 1988; Fons et al., Microbial Ecology in Health and Disease 2, 240-246, 2000).

Among the known intestinal pathogens is *Clostridium perfringens*, a strictly anaerobic Gram-positive bacterium, which is capable of sporulating and which is very widespread in the environment. This pathogen may arise from food, but may also be present in low concentration in the intestine and may begin to proliferate and to secrete toxins under the effect of a stress. The strains of *Clostridium perfringens* are classified into five toxinotypes as a function of the toxins they produce (Petit et al., Trends Microbiol. 7, 104-110, 1999). The strains of *C. perfringens* of type A and are responsible for gastrointestinal diseases in man. In 1997, more than 245 000 cases of infection with *C. perfringens* were recorded in the United States. This led to the hospitalization of 41 people, seven of whom died (Mead et al., Emerg. Infect. Dis. 5, 607-625, 1999). The strains of *C. perfringens* of type A and C may be, respectively, the cause of necrotic enteritis in pigs and poultry. In poultry, necrotic enteritis is a rapidly-evolving acute pathology whose mortality may reach 1% to 2% per day. In addition to its incidence on the well-being of the animals, this pathology may thus have an appreciable economic influence. Up to 1999, this disease was satisfactorily controlled by the use of antibiotics as growth factors. However, the European Union has banned their use in animal feed for fear of selecting resistant bacteria and thus of reducing the efficacy of the antibiotics in man. Since this ban, necrotic enteritis caused by *Clostridium perfringens* in pigs and poultry is no longer under control in Europe. The number of cases declared at the Réseau National d'Observations Epidémiologiques en Aviculture (RNOEA) (AFSSA Ploufragan) increased considerably in 1999 and 2000 (Valancony, Bulletin des GTV 12, 9-12, 2001).

At the present time, the search for alternative solutions for controlling and treating this disease is thus of primary importance.

*Ruminococcus gnavus* is a strictly anaerobic bacterium belonging to the family of Lachnospiraceae in the order of *Clostridiales.* Dabard et al. (Appl. Environ. Microbiol., 67, 4111-4118, 2001) showed that the strain *Ruminococcus gnavus* E1, isolated from the dominant flora in man, is capable of producing an antimicrobial substance, known as ruminococcin A or RumA, which accumulates in the culture supernatant. It is a bacteriocin belonging to the family of lantibiotics, active against various strains of pathogenic *Clostridium* sp. Gomez et al. (J. Bacteriol., 184, 18-28, 2002) have shown that the expression of genes involved in the biosynthesis of ruminococcin A is induced in the presence of trypsin. The same authors also showed that certain digestive enzymes might inhibit the induction of RumA production.

The inventors thus became interested in other bacteriocins.

The present invention relates to the peptides RumC1, RumC2 and RumC3 with antibacterial activity against *Clostridium perfringens*, and also to the genes coding for these peptides.

DESCRIPTION OF THE SEQUENCES

SEQ ID No. 1: Conserved peptide sequence of the RumC peptides of *Ruminococcus gnavus* E1

SEQ ID No. 2: Peptide sequence of the RumC peptides of *Ruminococcus gnavus* E1 determined experimentally by the Edman degradation method SEQ ID No. 3: Peptide sequence of the RumC peptides of *Ruminococcus gnavus* E1 determined experimentally by the Edman degradation method SEQ ID No. 4: Peptide sequence of the peptide RumC1 of *Ruminococcus gnavus* E1 deduced from SEQ ID No. 7

SEQ ID No. 5: Peptide sequence of the peptide RumC2 of *Ruminococcus gnavus* E1 deduced from SEQ ID No. 8

SEQ ID No. 6: Peptide sequence of the peptide RumC3 of *Ruminococcus gnavus* E1 deduced from SEQ ID No. 9

SEQ ID No. 7: Nucleotide sequence of the rumC1 gene of *Ruminococcus gnavus* E1

SEQ ID No. 8: Nucleotide sequence of the rumC2 gene of *Ruminococcus gnavus* E1

SEQ ID No. 9: Nucleotide sequence of the rumC3 gene of *Ruminococcus gnavus* E1

SEQ ID No. 10, 11 and 12: Experimentally determined peptide sequences

DESCRIPTION OF THE INVENTION

The present invention relates to a peptide with antimicrobial activity, characterized in that it comprises a peptide chosen from the following peptides: the peptide of the sequence SEQ ID No. 1, a peptide comprising a peptide having at least 80% identity with the polypeptide of SEQ ID No. 1, the peptide of the sequence SEQ ID No. 2, and a peptide comprising a peptide having at least 80% identity with the polypeptide of SEQ ID No. 2. According to one embodiment of the present invention, this peptide also comprises the peptide sequence SEQ ID No. 3. According to another embodiment of the present invention, this peptide comprises a peptide chosen from the peptides of sequence SEQ ID No. 4, 5 or 6.

The present invention also relates to a polynucleotide coding for antimicrobial activity, characterized in that it comprises a polynucleotide chosen from the polynucleotide according to any one of the sequences SEQ ID No. 7, 8 or 9, a polynucleotide that hybridizes to the polynucleotide according to any one of the sequences SEQ ID No. 7, 8 or 9 and a polynucleotide coding for a polypeptide as defined above.

The present invention also relates to an expression cassette, characterized in that it comprises in the transcription direction a promoter that is functional in a host organism, a polynucleotide as defined above and a terminator sequence in the same host organism.

The present invention further relates to a vector comprising a polynucleotide as defined above and/or an expression cassette as defined above.

The present invention also relates to a host organism transformed with a polynucleotide as defined above, an expression cassette as defined above and/or a vector as defined above.

The present invention relates to a strain of *Ruminococcus gnavus* deposited at the CNCM (Collection Nationale de Cultures de Microorganismes, Institut Pasteur, 25 rue du Docteur Roux, F-75015 Paris) on 19 December 2006 under the number CNCM I-3705, and also to a genetically unmodified bacterial strain in isolated form that produces a peptide as defined above.

The present invention relates to a protein mixture or fermentation must that may be obtained by a host organism or by the strain defined above.

The present invention also relates to a composition comprising a peptide as defined above, a host organism as defined above, a strain as defined above, a fermentation must of a host organism as defined above or a fermentation must of a strain as defined above. According to one embodiment of the present invention, the composition is in liquid form or in powder form.

The present invention also relates to a nutritional additive comprising a peptide as defined above, a host organism as defined above, a strain as defined above, a fermentation must of a host organism as defined above or a fermentation must as defined above. According to one embodiment of the present invention, the additive is in liquid form or in powder form.

The present invention also relates to an animal feed, characterized in that it comprises a nutritional base for animals and a nutritional additive as defined above.

The present invention also relates to the use of a peptide as defined above, of a host organism as defined above, of a strain as defined above, of a fermentation must of a host organism as defined above or of a fermentation must of a strain as defined above for the manufacture of a medicament, a nutritional additive or an animal feed. According to one embodiment of the present invention, this medicament or this nutritional additive is intended for preventing or treating necrotic enteritis in poultry or in pigs. According to another embodiment of the present invention, this medicament or this nutritional additive is intended for preventing or treating gastrointestinal diseases in man.

Finally, the present invention also relates to the nontherapeutic use of a peptide as defined above for treating animals. According to one embodiment of the present invention, the peptide is obtained from a strain endogenous to or from a strain exogenous to the animal. According to another embodiment of the present invention, the peptide is obtained from a strain endogenous to the animal and the production of the peptide by said endogenous strain is promoted. According to yet another embodiment of the present invention, the peptide is obtained from a strain endogenous to the animal and the growth of said endogenous strain is promoted.

Peptides

The present invention thus relates to peptides with antimicrobial activity. Preferably, these peptides are isolated from *Ruminococcus gnavus*, for example from a mutant strain of *Ruminococcus gnavus*. As a guide, these peptides may be isolated from the strain of *Ruminococcus gnavus* deposited at the CNCM (Collection Nationale de Cultures de Microorganismes, Institut Pasteur, 25 rue du Docteur Roux, F-75015 Paris) on 19 December 2006 under the number CNCM I-3705, i.e. the strain LEM 9-17.

The term "antimicrobial activity" means of the capacity to inhibit the growth or development of target bacteria or the capacity to kill target bacteria. The techniques for measuring antimicrobial activity are known to those skilled in the art. The antimicrobial activity is demonstrated in the present invention by a test of activity on the strain *Clostridium perfringens* CpA cultured on agar medium. The sample containing one of the peptides of the invention is placed in wells formed in the agar medium. The antimicrobial activity is demonstrated when an inhibition halo has formed around the well.

The peptide sequences of the peptides RumC1, RumC2 and RumC3 of *Ruminococcus gnavus* E1 are represented, respectively, by the sequences SEQ ID No. 4, SEQ ID No. 5 and SEQ ID No. 6. These sequences are deduced, respectively, from the nucleotide sequences of the genes rumC1, rumC2 and rumC3 represented, respectively, by the sequences SEQ ID No. 7, SEQ ID No. 8 and SEQ ID No. 9.

The invention also relates to fragments of these peptides RumC1, RumC2 and RumC3 of *Ruminococcus gnavus* E1, with antimicrobial activity. The term "peptide fragment" denotes a peptide comprising part but not all of the peptide from which it is derived. The invention thus relates to the peptides of the sequences SEQ ID No. 1, SEQ ID No. 2 and SEQ ID No. 3.

These fragments conserve their antimicrobial activity. The invention thus relates to the biologically active fragments. The term "biologically active fragment" denotes a fragment of a polypeptide that conserves the function of the polypeptide from which it is derived.

The invention also relates to peptides with antimicrobial activity that have at least 80%, 90%, 95%, 98% and preferentially at least 99% of amino acids identical to any of the peptides of the sequences SEQ ID No. 1, 2 or 3.

The methods for preparing the peptides of sequences SEQ ID No. 1, SEQ ID No. 2 and SEQ ID No. 3 are known to those skilled in the art.

The RumC peptides are secreted (or released) by the bacteria into the extracellular environment. It is possible that any of the peptides of sequences SEQ ID No. 4, 5 and/or 6 comprises a signal peptide for a given number of amino acids. In this case, the invention also relates to the mature peptide obtained after cleavage of the signal peptide. According to one embodiment of the present invention, the invention relates to peptides whose sequences are between position 20 and position 63 of the sequences SEQ ID No. 4, 5 and 6.

In another embodiment, the potential signal peptide of the peptide SEQ ID No. 4, 5 or 6 may be replaced with a heterologous signal peptide to perform the expression and secretion of this peptide by a heterologous host organism.

A subject of the invention is also a peptide with antimicrobial activity that has at least 80% identity with the peptide of SEQ ID No. 4, 5 or 6. According to one embodiment of the present invention, this peptide is isolated from a strain of *Ruminococcus gnavus*. According to another embodiment of the present invention, this peptide is isolated from other strains of *Ruminococcus* or from other bacteria. Alternatively, this peptide may be obtained via chemical synthesis.

One subject of the invention is a peptide that has at least 90%, 95%, 98% and preferentially at least 99% of amino acids identical to any of the peptides of the sequences SEQ ID No. 4, 5 or 6.

The term "identical amino acids" means amino acids that are invariant or unchanged between two sequences. These peptides may have a deletion, an addition or a substitution of at least one amino acid relative to the peptides represented by the sequences SEQ ID No. 4, 5 or 6. Amino acids modified after transcription, for example by dehydration, formation of monosulfide bridges, lanthionines, etc., are considered as amino acids that are unchanged between two sequences.

A subject of the invention is also peptides having at least 80%, 90%, 95%, 98% and preferentially at least 99% similarity with any of the peptides of the sequences SEQ ID No. 4, 5 or 6.

The term "similarity" means the measure of resemblance between protein or nucleic acid sequences. These peptides may have a deletion, an addition or a substitution of at least one amino acid relative to the peptides represented by the sequences SEQ ID No. 4, 5 or 6. The degree of similarity between two sequences, quantified by a score, is based on the percentage of identity and/or of conserving substitutions in the sequences.

The methods for measuring and identifying the degree of identity and the degree of similarity between polypeptides are known to those skilled in the art. Alignment of the sequences is performed, for example, by means of Vector NTi 9.1.0, the alignment program AlignX (Clustal W algorithm) (Invitrogen INFORMAX,) or using the tool CLUSTAW.

The peptides according to the invention may be isolated or purified from their natural environment. The peptides may be prepared via different processes. These processes are especially purification from natural sources such as bacteria that naturally express these peptides, the production of recombinant peptides by suitable host cells and their subsequent purification, production via chemical synthesis or, finally, a combination of these different approaches. Thus, the peptides of the sequences SEQ ID No. 1 to 6 of the present invention may be isolated from the strain of *Ruminococcus gnavus* deposited at the CNCM on 19 December 2006 under the number CNCM I-3705. In another embodiment, the peptides of the present invention are isolated from recombinant host organisms that express a RumC peptide according to the invention or a fragment of the RumC peptide with antimicrobial activity.

A subject of the invention is also fusion proteins, recombinant proteins or chimeric proteins comprising the peptides according to the invention.

The peptides of the invention may be isolated from the cecal content of monoxenic rats harboring the strain *Ruminococcus gnavus* E1 and from a mutant strain of *Ruminococcus gnavus*, more specifically the strain of *Ruminococcus gnavus* deposited at the CNCM on 19 December 2006 under the number CNCM I-3705. These peptides have antimicrobial activity, demonstrated by a test of activity on *Clostridium perfringens*.

Mass spectrometry enabled determination of the approximate molecular mass of the RumC peptide according to the invention. The molecular mass is between 4000 and 4600 Da and more specifically between 4100 and 4500 Da.

According to one embodiment of the present invention, the peptide is suitable for nutritional or pharmaceutical use, for example use in animal nutrition.

The term "peptide suitable for nutritional or pharmaceutical use" means a peptide whose characteristics are such that it is suitable for nutrition or pharmaceutics. The characteristics that are essential for nutritional or pharmaceutical use are especially the pH that the peptide can withstand. Specifically, the pH of the digestive system of man and animals is acidic, and it is thus essential that the peptide be resistant to this pH. Another essential characteristic for nutritional use is the temperature at which the antimicrobial substance is active. Specifically, the processing of an antimicrobial substance in a medicament, a nutritional additive or an animal feed, for example, involves treatments and a temperature above room temperature. The activity of the antimicrobials used must thus be stable under the conditions of the processes, especially the temperature conditions.

According to one embodiment of the present invention, the peptide or a peptide mixture according to the invention has antimicrobial activity at neutral pH and conserves its antimicrobial activity at an acidic pH, for example below 7 and preferably below 4.4.

According to one embodiment of the present invention, the peptide or a peptide mixture according to the invention has antimicrobial activity at 37° C. and conserves this activity at temperatures below and above room temperature, for example above 50° C.

The invention also relates to a peptide with antimicrobial activity, isolated from the cecal content of monoxenic rats or from a mutant strain of *Ruminococcus gnavus*, having activity against *Clostridium perfringens* strains, having a molecular mass of between 4000 and 4600 Da as determined by mass spectrometry, and being resistant to a pH of less than or equal to 7. According to one embodiment, the peptide comprises the sequence SEQ ID No. 1 and/or the sequence SEQ ID No. 2. According to another embodiment, it also comprises the peptide of the sequence SEQ ID No. 3. Advantageously, the peptide comprises a peptide chosen from any of the peptides having the sequence SEQ ID No. 4, 5 or 6.

The invention also relates to a peptide with antimicrobial activity, which may be obtained from a mutant strain of *Ruminococcus gnavus*, for example the strain of *Ruminococcus gnavus* deposited at the CNCM on 19 December 2006 under the number CNCM I-3705. According to one embodiment, the peptide has antimicrobial activity with regard to *Clostridium perfringens* strains. According to another embodiment, it has a molecular mass of between 4000 and 4600 Da and preferentially between 4100 and 4500 Da as determined by mass spectrometry. According to another embodiment, the peptide has antimicrobial activity at neutral pH and conserves its antimicrobial activity at an acidic pH, for example below 7 and preferably below 4.4. According to one embodiment, the peptide comprises the sequence SEQ ID No. 1 and/or the sequence SEQ ID No. 2. According to another embodiment, it also comprises the peptide of the sequence SEQ ID No. 3. Advantageously, the peptide comprises a peptide chosen from any of the peptides of sequence SEQ ID No. 4, 5 or 6.

The invention also relates to a peptide with antimicrobial potential isolated from the cecal content of monoxenic rats, corresponding to the chromatogram of FIG. 4A, obtained at 214 nm by reverse-phase HPLC, having activity against various strains of *Clostridium perfringens*, in particular of toxinotype A.

Polynucleotides

The invention also relates to polynucleotides coding for antimicrobial activity. Preferably, these polynucleotides code for antimicrobial activity of *Ruminococcus*.

According to the present invention, the term "polynucleotide" means a single-stranded polynucleotide chain or its complementary chain that may be of DNA or RNA type, or a double-stranded nucleotide chain that may be of complementary or genomic DNA type. Preferably, the polynucleotides of the invention are of DNA type, especially double-stranded DNA. The term "polynucleotide" also denotes modified polynucleotides.

The polynucleotides of the present invention may be isolated or purified from their natural environment. The polynucleotides of the present invention may also be prepared via chemical synthesis or via standard molecular biology techniques as described by Sambrook, Fristsch and Maniatis in their book entitled "Molecular cloning: a laboratory manual", edition: Cold Spring Harbor Laboratory Press, Cold Spring Harbor, N.Y., 1989.

The invention relates to the polynucleotide according to any of the sequences SEQ ID No. 7, 8 or 9. The invention also relates to the polynucleotide that hybridizes to the polynucleotide according to any of the sequences SEQ ID No. 7, 8 or 9. The invention also relates to the polynucleotide coding for a peptide with antimicrobial activity as defined above.

The invention also relates to a polynucleotide that has at least 80%, 85%, 90%, 95%, 98% and preferably at least 99% identity with the polynucleotide according to any one of the sequences SEQ ID No. 7, 8 or 9. This polynucleotide codes for antimicrobial activity. According to one embodiment, the polynucleotide codes for antimicrobial activity with regard to *Clostridium perfringens* strains.

The term "identical nucleotides" means nucleotides that are invariant or unchanged between two sequences. This polynucleotide may have a deletion, an addition or a substitution of at least one nucleotide relative to the reference polynucleotide.

The invention also relates to a polynucleotide that has at least 80%, 85%, 90%, 95%, 98% and preferably at least 99% similarity with the polynucleotide according to any one of the sequences SEQ ID No. 7, 8 or 9. This polynucleotide codes for antimicrobial activity. According to one embodiment, the polynucleotide codes for antimicrobial activity with regard to *Clostridium perfringens* strains.

The term "similarity" means the measure of resemblance between protein sequences or nucleic acid sequences. This polynucleotide may have a deletion, an addition or a substitution of at least one nucleotide relative to the reference polynucleotide. The degree of similarity between two sequences, quantified by a score, is based on the percentage of identity and/or of conserving substitution of the sequences.

The methods for measuring and identifying the degree of identity and the degree of similarity between nucleic acid sequences are known to those skilled in the art. Alignment of the sequences is performed, for example, by means of Vector NTi 9.1.0, the alignment program 35 AlignX (Clustal W algorithm) (Invitrogen INFORMAX,) or using the tool CLUSTAW.

The invention also relates to polynucleotides capable of selectively hybridizing with the polynucleotide according to any one of the sequences SEQ ID No. 7, 8 or 9. Preferably, the selective hybridization is performed under moderately stringent conditions and preferentially under highly stringent conditions. According to the invention, the term "sequence capable of selectively hybridizing" means sequences that hybridize with the reference sequence to a level significantly higher than the background noise. The level of the signal generated by the interaction between the sequence capable of selectively hybridizing and the reference sequences is generally 10 times and preferably 100 times stronger than that of the interaction of the other DNA sequences that generate the background noise. The conditions of stringent hybridization that allow a selective hybridization are known to those skilled in the art. In general, the hybridization and washing temperature is at least 5° C. below the Tm of the reference sequence at a given pH and for a given ionic strength. Typically, the hybridization temperature is at least 30° C. for a polynucleotide of 15 to 50 nucleotides and at least 60° C. for a polynucleotide of more than 50 nucleotides. By way of example, the hybridization is performed in the following buffer: 6×SSC, 50 mM Tris-HCl (pH 7.5), 1 mM EDTA, 0.02% PVP, 0.02% Ficoll, 0.02% BSA, 500 μg/ml denatured salmon sperm DNA. The washes are performed, for example, successively at low stringency in a 2×SSC, 0.1% SDS buffer, at moderate stringency in a 0.5×SSC, 0.1% SDS buffer and at high stringency in a 0.1×SSC, 0.1% SDS buffer. The hybridization may, of course, be performed according to other common methods known to those skilled in the art (see especially Sambrook, Fristsch and Maniatis in their book entitled "Molecular cloning: a laboratory manual", edition: Cold Spring Harbor Laboratory Press, Cold Spring Harbor, N.Y., 1989). Preferably, the polynucleotides that selectively hybridize to a reference polynucleotide conserve the function of the reference sequence. In the present case, the polynucleotides that selectively hybridize with the polynucleotide according to any one of the sequences SEQ ID No. 7, 8 or 9 code for antimicrobial activity.

The invention relates generally to polynucleotides coding for the peptides according to the invention. On account of the degeneracy of the genetic code, different polynucleotides may code for the same polypeptide.

Expression Cassettes

According to one embodiment of the invention, a polynucleotide coding for a peptide according to the invention is inserted into an expression cassette using cloning techniques that are well known to those skilled in the art. This expression cassette comprises the elements necessary for the transcription and translation of the coding sequences for the polypeptides according to the invention.

Advantageously, this expression cassette comprises both elements for producing a peptide via a host cell and elements necessary for regulating this expression.

These expression cassettes comprise, in the transcription direction:

a promoter that is functional in a host organism;

a polynucleotide according to the invention;

a terminator sequence that is functional in the same host organism.

Any type of promoter sequence may be used in the expression cassettes according to the invention. The choice of promoter will depend especially on the host organism chosen for the expression of gene of interest. Certain promoters allow constitutive expression, whereas other promoters are, on the other hand, inducible.

Among the functional promoters in fungi, mention will be made especially of that of glyceraldehyde-3-phosphate dehydrogenase from *Aspergillus nidulans* (Roberts et al., Current Genet. 15, 177-180, 1989).

Among the functional promoters in bacteria, mention will be made especially of that of RNA polymerase from the bacteriophage T7 (Studier et al., Methods in Enzymology, 185, 60-89, 1990).

Among the functional promoters in yeasts, mention will be made of the promoter of the gene GAL1 (Elledge et al., Proc. Natl Acad. Sciences, USA. 88, 1731-1735, 1991) or of the Gal4 and ADH promoters of *S. cerevisiae*. All these promoters are described in the literature and well known to those skilled in the art.

For expression in *Penicillium funiculosum*, expression cassettes comprising an H4B histone promoter, an aspartic acid protease promoter or a csl13 promoter (WO 00/68401) will be chosen, for example.

For expression in the yeast *Pichia pastoris*, expression cassettes comprising the methanol-inducible AOX1 promoter (Tschopp et al., Biotechnology, 5, 1305-1308, 1987) or the GAP strong constitutive promoter (Waterham et al., Gene 186, 37-44, 1997) will be chosen, for example.

For expression in *Schizosaccharomyces pombe*, expression cassettes comprising the Nmt1 regulation promoter repressed by thiamine and activated in the absence of thiamine (Maundrell, J. Biol. Chem. 265, 10857-10864, 1989) will be chosen, for example.

The expression cassettes according to the present invention may also include any other sequence necessary for the expression of polypeptides or polynucleotides, for instance regulation elements or signal sequences allowing the secretion of the polypeptides produced by the host organism. It is especially possible to use any regulation sequence that makes it possible to increase the level of expression of the coding sequence inserted into the expression cassette. According to the invention, it is especially possible to use, in combination with the promoter regulation sequence, other regulation sequences, which are located between the promoter and the coding sequence, such as transcription activators ("enhancers").

In addition, the expression cassettes according to the present invention may include any other sequence necessary for the secretion of the polypeptides produced by the host organism, such as signal sequences. For the secretion by *Pichia pastoris*, it is possible, for example, to use the a factor sequence as the secretion signal.

A wide variety of terminator sequences may be used in the expression cassettes according to the invention, these sequences allowing the termination of transcription and the polyadenylation of mRNA. Any terminator sequence that is functional in the selected host organism may be used.

For expression in *Penicillium funiculosum*, expression cassettes comprising an H4.B histone terminator, an aspartic acid protease terminator or a csl13 terminator (WO 00/68401) will be chosen, for example.

A subject of the present invention is also a polynucleotide comprising an expression cassette according to the invention; advantageously, the expression cassettes according to the present invention are inserted into a vector.

Vectors

The present invention also relates to cloning or expression vectors for the transformation of a host organism comprising at least one polynucleotide or an expression cassette according to the present invention. This vector may especially correspond to a plasmid, a cosmid, a bacteriophage or a virus into which is inserted a polynucleotide or an expression cassette according to the invention. The techniques for constructing these vectors and for inserting a polynucleotide of the invention into these vectors are known to those skilled in the art. In general, any vector capable of maintaining itself, of self-replicating or of propagating in a host cell in order especially to induce the expression of a polynucleotide or a peptide may be used. A person skilled in the art will select the appropriate vectors as a function of the host organism to be transformed, and as a function of the transformation technique used.

The vectors of the present invention are used especially for transforming a host organism for the purpose of replicating the vector and/or of expressing a peptide according to the invention in the host organism.

The invention also relates to a method for preparing a peptide according to the invention, comprising the following steps:

a host organism is transformed with an expression vector comprising an expression cassette according to the invention and/or with a polynucleotide according to the invention, the peptides produced by the host organism are isolated.

Host Organisms

A subject of the present invention is also a process for transforming a host organism by integration into said host organism of at least one polynucleotide, of at least one expression cassette or of at least one vector according to the invention. The polynucleotide may be integrated into the genome of the host organism or may be stably replicated in the host organism. The methods for transforming host organisms are known to those skilled in the art and widely described in the literature.

The present invention also relates to a host organism transformed with a polynucleotide, an expression cassette or a vector according to the invention.

According to the invention, the term "host organism" in particular means any higher or lower monocellular or multicellular organism, chosen in particular from bacteria, yeasts and fungi. In particular, the term "host organism" means a nonhuman organism. Advantageously, the yeasts are chosen, for example, from *Pichia pastoris, Saccharomyces cerevisiae, Yarrowia lipolytica* and *Schwanniomyces occidentalis*. The fungi are chosen, for example, from *Aspergillus, Trichoderma* and *Penicilliums*, preferentially from *Penicillium funiculosum, Trichoderma reesei, Aspergillus niger, Aspergillus awamori, Aspergillus kawachii* and *Trichoderma koningii*. In one embodiment of the invention, the host organism is a strain of *Penicillium funiculosum* in which a peptide according to the invention is expressed or overexpressed. In another embodiment, the host organism is strain of *Debaromyces castellii* in which a peptide according to the invention is expressed or overexpressed. In yet another embodiment, the host organism is strain of *Ruminococcus gnavus* in which a peptide according to the invention is expressed or overexpressed.

The techniques for constructing vectors, for transforming host organisms and for expressing heterologous proteins in these organisms are widely described in the literature, especially by Sambrook, Fristsch and Maniatis in the book entitled "Molecular cloning: a laboratory manual", edition: Cold Spring Harbor Laboratory Press, Cold Spring Harbor, N.Y., 1989 or by Ausubel et al. in the book entitled "Current Protocols in Molecular Biology", edition: Greene Publishing Associates, Inc., and John Wiley and Sons, NY, 1992.

Strains

The novel strain of *Ruminococcus gnavus* was deposited at the CNCM (Collection Nationale de Cultures de Microorganismes, Institut Pasteur, 25 rue du Docteur Roux, F-75015 Paris) on 19 December 2006 under the number CNCM I-3705. The CNCM is an international depository authority according to Article 7 of the Treaty of Budapest.

The novel strain was obtained by random mutagenesis of the strain *R. gnavus* L14. This strain is a spontaneous mutant of *R. gnavus* E1 that has lost the capacity to produce RumA in vitro but that still synthesizes RumC in vivo. A powerful alkylating agent, N-methyl-N'-Nitro-N-nitrosoguanidine (NG) was used for the mutagenesis. No genetic modification was obtained via recombinant techniques using a DNA or an RNA of another origin.

The culture medium of strain LEM 9-17 is preferably BHI medium supplemented with yeast extract and with hemin (BHI-YH).

Protein Mixture, Fermentation Must

The invention also relates to a process for preparing a peptide with antimicrobial activity according to the invention, said process comprising the following steps:

a) culturing a strain of *Ruminococcus gnavus* or a transformed host organism according to the invention under conditions that induce expression of the peptide, and
b) recovering the culture supernatant comprising the peptide.

Separation of the peptide from the culture supernatant may be performed via the charge, the size and/or the hydrophobic nature. A person skilled in the art knows the various techniques for separation as a function of the charge, the size and/or the hydrophobic nature of the various constituents of a medium.

This culture supernatant or fermentation must can then be concentrated or lyophilized for the formulation of a food additive or an animal feed. The process may comprise additional steps of purification of the antimicrobial substance from the culture supernatant.

If the host organism does not secrete the antimicrobial substance into the culture medium, an additional step of cell lysis and of purification of the cell extract may be necessary.

The peptides of the invention may also be obtained from the cecal content of monoxenic rats.

Composition

The compositions according to the invention comprise a peptide according to the invention, a host organism according to the invention, a strain according to the invention, a fermentation must of a host organism according to the invention or a fermentation must of a strain according to the invention. The compositions are in liquid form or in powder form. These compositions comprise various ingredients.

The liquid compositions may comprise, for example, another antimicrobial agent, for example sorbic acid or a sorbic acid salt, benzoic acid or a benzoic acid salt, or fumaric acid or a fumaric acid salt. The compositions of the invention may also comprise sorbitol. Sorbitol is a stabilizer and a formulating agent. The compositions of the invention may also comprise antifreezes, for example ethylene glycol, glycerol, propylene glycol and 1,2-propanediol.

The compositions in powder form comprise a support. This support may be chosen from wheat flour, starch, maltodextrin, gypsum and corn cobs.

The compositions according to the invention have antimicrobial activity. They provide alternative solutions to the use of antibiotics. They may be used, for example, in animal rearing or as medicaments for man.

The compositions of the present invention comprise at least one peptide according to the invention, but they may also comprise other substances, for instance vitamins, other active principles, amino acids or mineral salts.

The compositions according to the invention make it possible, for example, to prevent or treat necrotic enteritis in pigs or poultry and to prevent or treat gastrointestinal diseases in man.

The compositions of the invention are, for example, added to animal feed or are, for example, combined with a nutritional base. The present invention thus also relates to animal feed comprising a composition according to the invention. This feed is usually in the form of flour or granules into which are incorporated the compositions with antimicrobial activity. A subject of the present invention is also animal feed comprising a peptide according to the invention, a host organism according to the invention or a fermentation must/culture supernatant of a host organism according to the invention.

The term "feed" means anything that can serve as food for animals. The term "nutritional base" means anything that constitutes the essential part of the food ration of the animal, constituted, for example, by a mixture of cereals, proteins and fats of animal and/or plant origin. Usually, these nutritional bases comprise, for example, corn, wheat, pea and soybean. These nutritional bases are adapted to the needs of the various animal species for which they are intended. They may be, for example, poultry (laying hens, broiler chickens, turkeys and ducks) or pigs (growing and finishing pigs, or piglets).

Use of the Peptides

The present invention also relates to the use of a peptide according to the invention, of a host organism according to the invention, of a strain according to the invention, of a fermentation must of a host organism according to the invention or of a fermentation must of a strain according to the invention for the manufacture of a medicament.

The present invention also relates to the use of a peptide according to the invention, of a host organism according to the invention, of a strain according to the invention, of a fermentation must of a host organism according to the invention or of a fermentation must of a strain according to the invention as a nutritional additive or, in combination with other compounds, as animal feed.

According to one embodiment of the present invention, this medicament or this nutritional additive is intended for preventing or treating necrotic enteritis in pigs or poultry.

According to one embodiment of the present invention, this medicament or this nutritional additive is intended for preventing or treating gastrointestinal diseases in man.

DESCRIPTION OF THE FIGURES

FIG. 7A: SN 9-17

FIG. 7B: active CM fraction

FIG. 7C: R 10 kDa

EXAMPLES

Materials and Methods

1. Bacterial Strains and Culture Media

Figure 1:
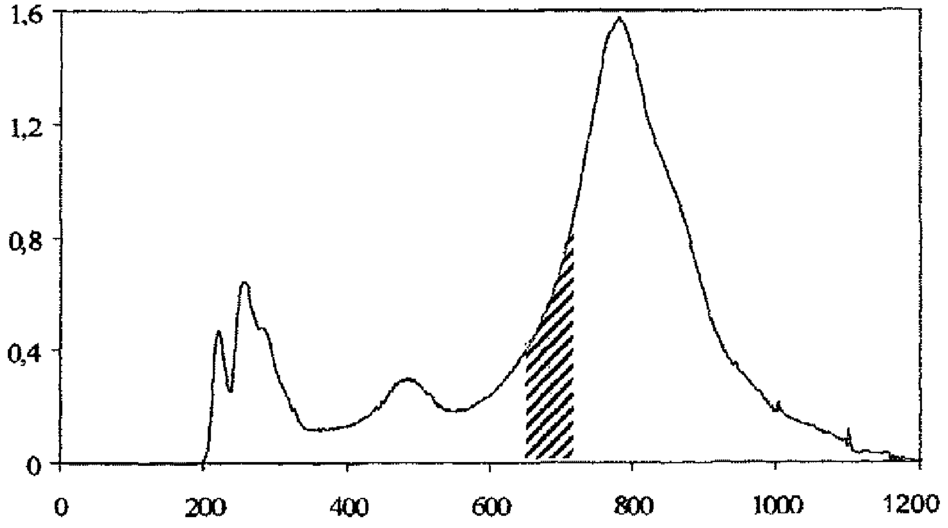
FIG. 1: chromatogram obtained by molecular screening on Sephadex G-75 of the soluble fraction contained in 10 g of cecal content from monoxenic rats harboring the strain *R. gnavus* E1; the x-axis gives the elution volume in mL; the y-axis gives the absorption at 280 nm; the shaded area corresponds to the fractions that are active against *C. perfringens* (fractions 325 to 358)

The strain *Ruminococcus gnavus* E1, which produces RumC, was isolated from the dominant fecal microbiota of a healthy adult (Dabard et al., Appl. Environ. Microbiol., 67, 4111-4118, 2001). The strain *R. gnavus* L14 is a spontaneous mutant of *R. gnavus* E1 that has lost the capacity to produce RumA in vitro but that still synthesizes RumC in vivo.

The *Ruminococcus gnavus* strain deposited at the CNCM on December 2006 under the number CNCM I-3705 is derived from random mutagenesis of the strain L14. It is capable of producing RumC in vitro, on trypsin-supplemented agar medium (500 µg/ml; but not in liquid medium). It is the strain LEM 9-17.

The strain used as target for the activity tests is the strain *Clostridium perfringens* CpA (Dabard et al., Appl. Environ. Microbiol., 67, 4111-4118, 2001).

These four strains are cultured anaerobically, in a chamber of "Freter" type under a controlled atmosphere (85% $N_2$, 10% $H_2$, 5% $CO_2$). They are incubated at 37° C. in BHI medium supplemented with yeast extract and with hemin (BHI-YH).

Liquid BHI-YH:

37 g/L of BHI (Brain Heart Infusion, Difco Laboratories)

5 g/L of yeast extract (Yeast Extract, Fluka)

5 mg/L of hemin (Hemin, Sigma)

agar BHI-YH:

idem+15 g/L of agar (BACTO™ agar, Difco Laboratories)

2. Antimicrobial Activity Tests Using a Liquid Sample

To perform an antimicrobial activity test using a liquid sample, $10^4$ to $10^5$ *C. perfringens* CpA cells are plated out on agar medium. After 30 minutes at room temperature, wells 6 mm in diameter are made in the agar using a Pasteur pipette. The samples, less than 100 µL in volume, are then placed in the wells and the dishes are incubated for 16 to 24 hours at 37° C. If the sample contains an antimicrobial substance directed against *C. perfringens* CpA, the growth of the bacteria is inhibited, which leads to the formation of an "inhibition halo" around the well.

The activity tests may also be performed by directly placing 10 µL of the test sample onto agar preinoculated with *C. perfringens.*

3. Antimicrobial Activity Test Using Colonies That Grow in Agar Medium

After culturing for 24 hours on agar medium supplemented or otherwise with 50 µg/mL of trypsin, the strain potentially producing an antimicrobial substance is covered with "soft" agar medium (containing 7.5 g of agar/L) containing the target strain. This soft agar is prepared by extemporaneously mixing 5 mL of superfused agar medium with 5 mL of liquid medium containing $10^4$ to $10^5$ cells of the target strain. The Petri dishes are then reincubated for 16 to 24 hours at 37° C. An inhibition halo is observed around the colonies that produce an antimicrobial substance.

4. Removal of the Cell Debris and Food Residues From the Cecal Content 10 g of cecal content are diluted in 30 mL of PBS (NaCl 137 mM, KCl 2.68 mM, $Na_2HPO_4$ 8.1 mM, $KH_2PO_4$ 1.47 mM, pH 7.4) and then centrifuged at 10 000×g and at 4° C. for 15 minutes. The pellet containing the cell debris and the food residues is removed.

5. Centrifugation Filtration Units

These are filter membranes for separating proteins into two fractions, as a function of their molecular mass after centrifugation. These systems may also be used for concentrating or desalting samples.

Several manufacturers sell products of this type. In most cases, the membranes are made of regenerated cellulose, but they may also be made of polyethersulfone. The choice of the system is made as a function of the volume of the samples to be treated and of the cut-off threshold of the membranes (Table 1). These filtration units were used according to the instructions provided by the manufacturer for the choice of the type of rotor and the centrifugation speed. However, the centrifugation times were variable as a function of the viscosity of the sample.

TABLE 1

Characteristics of the filtration units used in the course of the RumC purification tests

| Name | Type of membrane | Cut-off threshold | Maximum volume |
|---|---|---|---|
| Amicon ® Ultra-15 PL-5* | Regenerated cellulose | 5 kDa | 20 mL |
| Microcon ® YM-10* | Regenerated cellulose | 10 kDa | 0.5 mL |
| Microcon ® YM-3* | Regenerated cellulose | 3 kDa | 0.5 mL |
| Vivaspin 500-5000MWCO** | Polyethersulfone | 5 kDa | 0.6 mL |
| Vivaspin 500-3000MWCO** | Polyethersulfone | 3 kDa | 0.6 mL |

*product of the brand name Millipore;
**product of the brand name Sartorius

6. Molecular Screening on Sephadex G-75

Molecular screening of the supernatant of the cecal content is performed on a column of Sephadex G-75 (2.4×187 cm). The sample (the volume of which is about 2% of the volume of the column) is deposited on the column, the elution being performed at 4° C. at a flow rate of 1 mL/minute using PBS and 600 2-mL fractions are collected. A chromatogram is obtained by reading the absorption at 280 nm of each fraction.

7. Molecular Screening on FPLC

Molecular screening of the active CM fraction is performed on the FPLC system. The sample is loaded onto a HiLoad 26/60 Superdex 30 pg column (GE Healthcare). The elution is performed at a flow rate of 2.5 mL/minute with PBS. The protein material eluted is detected by measuring the variation in absorption at 280 nm. The fractions corresponding to 2 minutes of elution are collected automatically.

8. HPLC on a Cation-Exchange CM Column

Cation-exchange HPLC is performed on a Waters 600S Controller equipped with a Waters 616 Pump injector. The sample (0.5 mL) is loaded onto a CM-3SW Spherogel semi-preparative column from TSK. The elution is performed at pH 5 in a 20 mM sodium acetate buffer and at a flow rate of 0.8 mL/minute, using an NaCl concentration gradient from 0 to 1 M. During the first 20 minutes, the elution is performed in isocratic mode without NaCl and then with a linear NaCl concentration gradient from 0 to 0.5 M for 30 minutes. The elution then continues for 5 minutes under isocratic conditions, then a jump to an NaCl concentration of 1 M is performed over 1 minute, before continuing for 15 minutes under isocratic conditions and, finally, returning to the initial conditions. The protein material eluted is detected by measuring the absorption at 280 or 214 nm using a Waters 486 Tunable Absorbance Detector. The fractions are collected automatically and then desalted using the Amicon® Ultra PL-5 systems.

9. FPLC on a Cation-Exchange Column

Cation-exchange chromatographies are performed on an FPLC chain. The sample is loaded onto a Hi-Prep 16/10 CM FF column (GE Healthcare). The elution is performed at pH 5 in a 20 mM sodium acetate buffer, using an NaCl concentration gradient from 0 to 0.4 M. The elution is performed for 50 minutes in isocratic mode without NaCl, at a flow rate of 2 mL/minute. The elution then continues at a flow rate of 5 mL/minute with a linear NaCl concentration gradient from 0 to 0.4 M over 40 minutes. The protein material eluted is detected by measuring the variation in absorption at 280 nm. 1 mL fractions are collected automatically and then desalted on Sep-Pak® C18 cartridges.

10. Reverse-Phase HPLC

Reverse-phase HPLC is performed on an Alliance Waters 1690 Separations Module chain. The sample (100 μL) acidified beforehand with 0.1% trifluoroacetic acid (TFA) is loaded onto a Vydac 218TP52 250×2 analytical column. The elution is performed at a constant flow rate (0.5 mL/minute). After elution for 10 minutes in isocratic mode at 15% acetonitrile, a linear gradient of 15% to 30% acetonitrile is applied over 60 minutes. A jump to 70% acetonitrile is then performed over 1 minute and the elution continues for 19 minutes under isocratic conditions, before returning to the initial conditions. The protein material eluted is detected by measuring the variation in absorption at 214 nm using a Waters 996 Photodiode Array Detector. 0.5 mL fractions are collected automatically. The acetonitrile is evaporated off using a Speed Vac Concentrator (Savant).

11. Mass Spectrometry

The mass spectrometry analyses were performed at the Timone proteomic plateau (School of Pharmacy, Marseilles, France).

The mass spectra of Maldi type were obtained on an Ettan Maldi-Tof Pro spectrometer (GE Healthcare, Uppsala, Sweden) used in positive linear mode with delayed extraction. The samples are co-crystallized with a 5 mg/mL solution of α-cyano-4-hydroxycinnamic acid on the Maldi target via the dry drop method. The spectra are acquired with an acceleration potential of 20 kV and a laser power set to the minimum level in order to obtain a good signal. Calibration of the spectra is obtained in external mode via acquisition of a standard mixture of peptides of known masses (Pepmix4, Laserbiolabs, Nice, France).

For certain samples that are difficult to crystallize, the co-crystallization is performed using a solution of 2,5-dihydroxybenzoic acid.

12. Edman Sequencing

This technique is based on the reaction of a free terminal amine group of a protein with phenyl isothiocyanate ($C_6H_5N{=}C{=}S$). This cyclic compound performs a nucleophilic attack in basic medium on the first amino acid residue of the protein. The phenylthiocarbamyl (PTC) derivative of the peptide is then cleaved off by hydrolysis. The anilinothiazolinone (ATZ) of the first amino acid and the protein having lost this amino acid are obtained. The ATZ-amino acid is then converted into phenylthiohydantoin-(PTH) amino acid.

The PTH-amino acids successively obtained are separated and identified by RP-HPLC by measuring the absorption at 280 nm and by comparing the elution times.

The reaction cycle may be repeated and thus leads to the sequence of the protein.

13. Random Mutagenesis

A culture of 14 mL of the strain L14 incubated for 24 hours at 37° C. is divided into seven 2 mL tubes and the tubes are then centrifuged at 5800×g for 10 minutes. The cell pellets are washed twice with 2 mL of 0.1 M citrate buffer (citric acid 21 mg/mL, NaOH 8.8 mg/mL, pH 5.5) and then taken up in citrate buffer containing increasing concentrations of N-methyl-N'-nitro-N-nitrosoguanidine (NG), a powerful mutagenic agent.

TABLE 2

| Volumes of the solutions used during desalting on Sep-Pak | | | | | | | |
|---|---|---|---|---|---|---|---|
| | Tubes | | | | | | |
| | 1 ($T_0$) | 2 | 3 | 4 | 5 | 6 | 7 |
| [NG] final in μg/mL | 0 | 25 | 50 | 100 | 200 | 400 | 1000 |

The tubes are then incubated for 30 minutes at 37° C., before being centrifuged for 10 minutes at 5800×g. The pellet is washed with 0.1 M phosphate buffer ($KH_2PO_4$ 13.6 mg/mL, NaOH 2.32 mg/mL, pH 7) and then taken up in liquid BHI-YH medium.

14. Desalting on Sep-Pak® C18 Cartridges (Waters)

According to the models, these columns are in the form of syringes into which the phase is poured, or of mini-columns fixed to the end of a syringe. The flow of the buffers is ensured by a peristaltic pump. In a first stage, the column is equilibrated by passing $H_2O$ and then $CH_3CN$ and finally $H_2O$ containing 0.05% TFA. The sample, acidified beforehand with 0.05% TFA, is then applied. The elution is performed in three steps, by successive addition of $H_2$—0.05% TFA, 40% $CH_3CN$—0.05% TFA and $CH_3CN$—0.05% TFA.

Three fractions are thus collected: the fraction corresponding to the protein not retained by the column and to the salts (fraction NR), the fraction containing the protein diluted with 40% $CH_3CN$ (40% ACN fraction) and the fraction containing the protein diluted with 100% $CH_3CN$ (100% ACN fraction). The solvent is evaporated off using a Speed Vac Concentrator or a rotavapor, depending on the volume.

Table 3 indicates the volumes of each solution used for the desalting of fractions obtained from the purification of RumC (cf. Results and discussion). These volumes depend on the phase volume of the Sep-Pak.

TABLE 3

| Volumes of the solutions used during Sep-Pak as a function of the applications | | | |
|---|---|---|---|
| | | Desalting of: | |
| | Volume of: | SN 9-17 | Active CM fraction |
| | Phase | 12 mL | 1 mL |
| Equilibration | $H_2O$ | 20 mL | 5 mL |
| | $CH_3CN$ | 20 mL | 5 mL |
| | $H_2O$-0.05% TFA | 30 mL | 5 mL |
| Elution | Sample | 30-35 mL | 50 mL |
| | $H_2O$-0.05% TFA | 30-35 mL | 15 mL |
| | 40% $CH_3CN$-0.05% TFA | 20 mL | 6 mL |
| | $CH_3CN$-0.05% TFA | 20 mL | 4 mL |

15. Test of Temperature Resistance

Aliquot portions of a fraction containing RumC are heated, each to a different temperature, using a heating block for 5 or 15 minutes, and then stored at 4° C. They are then subjected to an antimicrobial activity test.

16. Test of pH Resistance

Aliquot portions of a fraction containing RumC are diluted approximately tenfold in the desired buffer. After 10 minutes at room temperature, each solution is deposited on a Vivaspin 500 3 kDa filtration unit and then centrifuged according to the manufacturer's instructions. The buffer is added to the fraction retained by the Vivaspin 500, and the filtration unit is then recentrifuged. The volume of each of the fractions retained by the Vivaspin 500 3 kDa, i.e. containing RumC, is adjusted with buffer to correspond to the starting volume. The various fractions are then stored at 4° C. before being subjected to an antimicrobial activity test.

The Vivaspin 500 3 kDa filters do not withstand pH values of greater than 9. Only buffers of acidic or neutral pH were thus tested. The composition is as follows:

pH 2 buffer: 50 mM KCl—13 mM HCl pH 4.4 buffer: 0.2 M pH 4.4 sodium acetate buffer pH 7 buffer: 50 mM $KH_2PO_4$—39 mM NaOH Results and Discussion 1. Purification of RumC From Cecal Content Although the strain *Ruminococcus gnavus* E1 is culturable, RumC is not produced in vitro under the culture conditions tested. To purify RumC, it is thus necessary to work using cecal content from monoxenic rats that harbor the strain E1 or to create a mutant strain of *R. gnavus* capable of producing RumC in vitro (see section 2).

1.1. Dilution of Cecal Content Form Monoxenic Rats

The first step consisted in diluting the cecal content in PBS.

1.2. Removal of the Cell Debris

During the second step of purification, the bacteria, the cell debris and the food residues are removed by centrifugation of the cecal content.

1.3. Concentration

The solution is then concentrated on the Amicon Ultra-15 PL-5 system, before being applied to a molecular screening column.

1.4. Antimicrobial Activity Test

All the fractions obtained were tested on the strain *C. perfringens* CpA, which confirmed the presence of an anti-*C. perfringens* substance in the cecal content of the monoxenic rats.

A negative control was performed with cecal content from axenic rats (microorganism-free). No anti-*C. perfringens* activity was detected. The anti-*C. perfringens* substance present in the cecal content of the monoxenic rats is thus indeed specific to *R. gnavus* E1.

Thereafter, each purification test was followed by anti-*C. perfringens* activity tests. In a first stage, only the presence or absence of the activity was studied, taking care to ensure that the negative results were not associated with the sensitivity threshold of the technique. Quantitative tests were performed in a second stage, when the definitive protocol was established.

1.5. Molecular Screening on a Sephadex G-75 Column

Molecular screening was performed on a Sephadex G-75 column (2.4×187 cm). The elution was monitored by reading the absorption at 280 nm of each of the 600 2-mL fractions collected.

Antimicrobial activity tests were performed on the fractions concentrated beforehand using Microcon® YM-3.

Fractions 325 to 358 proved to be active against *C. perfringens* and were pooled to form the new active GF fraction (shaded area of FIG. 1).

A control performed with cecal content from axenic rats led to an elution profile comparable to that obtained with the cecal content from monoxenic rats, but no anti-*C. perfringens* activity could be detected.

1.6. Evaluation of the Size of RumC

Figure 2A:
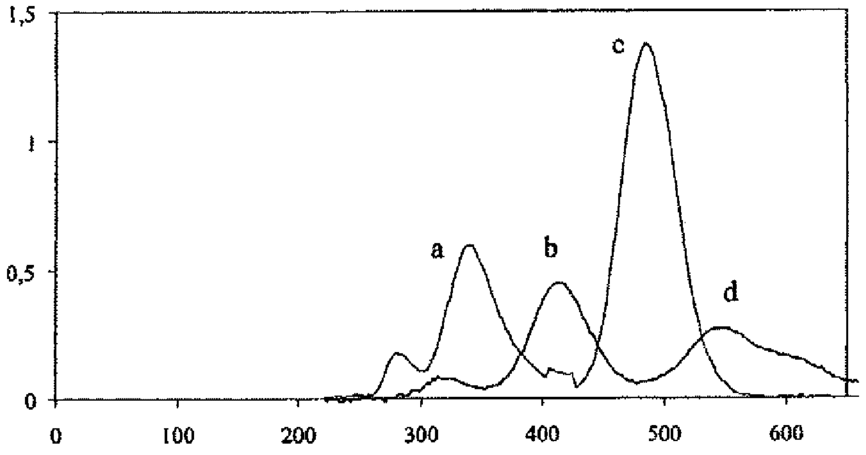
FIG. 2A: chromatogram obtained by molecular screening of standard proteins on Sephadex G-75; the x-axis gives the elution volume in mL; the y-axis gives the absorption at 280 nm; a: albumin 67 kDa; b: ovalbumin kDa; c: chymotrypsin 25 kDa; d: ribonuclease A 13.7 kDa
Figure 2B:
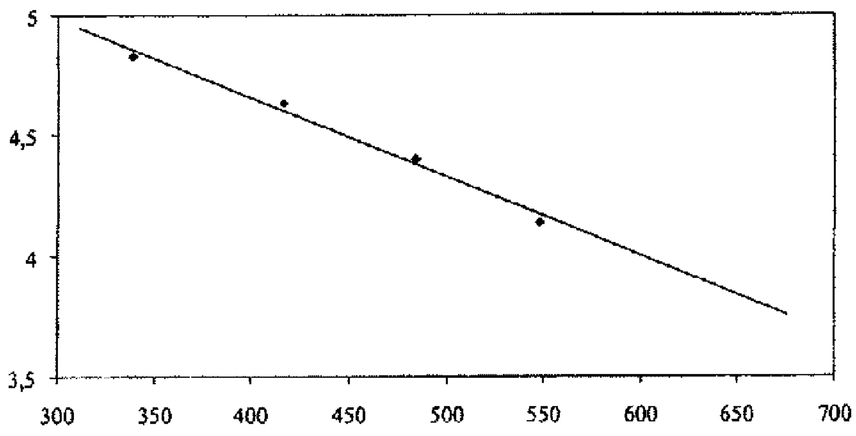
FIG. 2B: log calibration curve (MM)=f(Ve) obtained from the chromatograms of FIG. 2A; the x-axis gives the elution volume in mL; the y-axis gives the molecular mass logarithm

In order to evaluate the size of RumC present in the active GF fraction, standard proteins of known molecular masses were deposited on the same Sephadex G-75 column and the respective elution volumes were measured (FIG. 2A). A calibration curve defining the proportionality between the logarithm of the molecular mass (log (MM)) of a substance and its elution volume (Ve) was then plotted (FIG. 2B). With a mean elution volume of 683 mL, the antimicrobial substance is not within the range of the chosen standard proteins, but by extrapolation, its molecular mass could be approximately evaluated as 5200 Da.

1.7. Chromatography on a Cation-Exchange Resin

Figure 3:
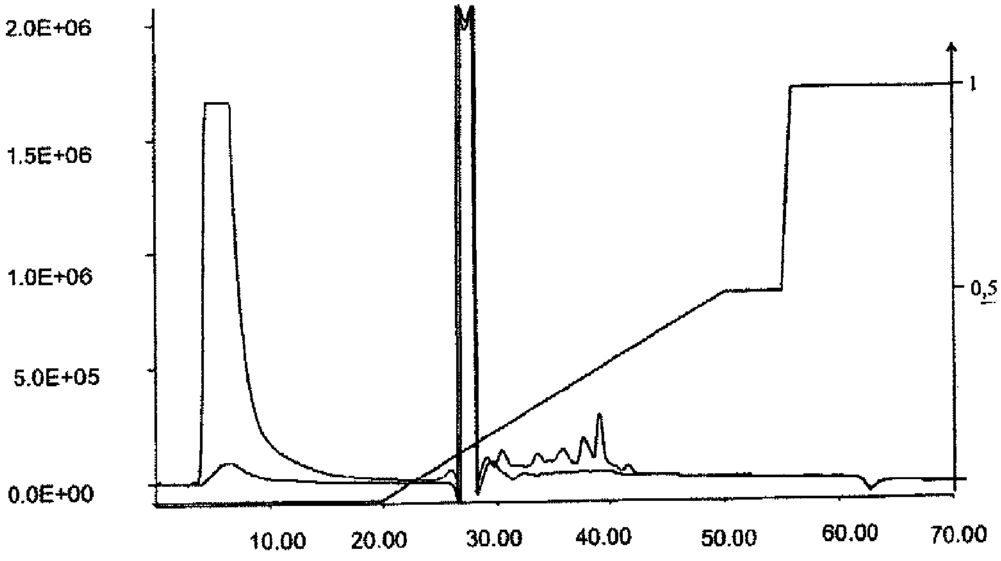
FIG. 3: chromatogram obtained by HPLC on a cation-exchange column of the active GF fraction; the y-axis, left-hand side, gives the absorption at 214 nm; the y-axis, right-hand side, gives the NaCl concentration in M; the x-axis gives the time in minutes

Using the active GF fraction, a cation-exchange chromatography on a carboxymethyl (CM)—Spherogel™ column was envisioned using an HPLC system. The elution was performed via an NaCl concentration gradient, at pH 5, and monitored at 214 nm (FIG. 3).

The activity is found between minutes 32 and 38 (active CM fraction), which corresponds to an NaCl concentration of 0.2 to 0.3 M. This technique made it possible to eliminate contaminants in the fraction not retained, especially all the yellow pigments.

Analysis of the active CM fraction by mass spectrometry shows that it contains a single peptide of about 4200 Da (result not shown).

This fraction was subjected to N-terminal sequencing. The first 11 amino acids were thus determined: AGVIX(N/S) GTXAV (SEQ ID No. 10). This sequence does not show any strong homology with known proteins.

The sequencing also revealed two minor sequences.

1.8. Reverse-Phase HPLC Chromatography

Various absorption peaks at 214 nm were obtained.

Figure 4:
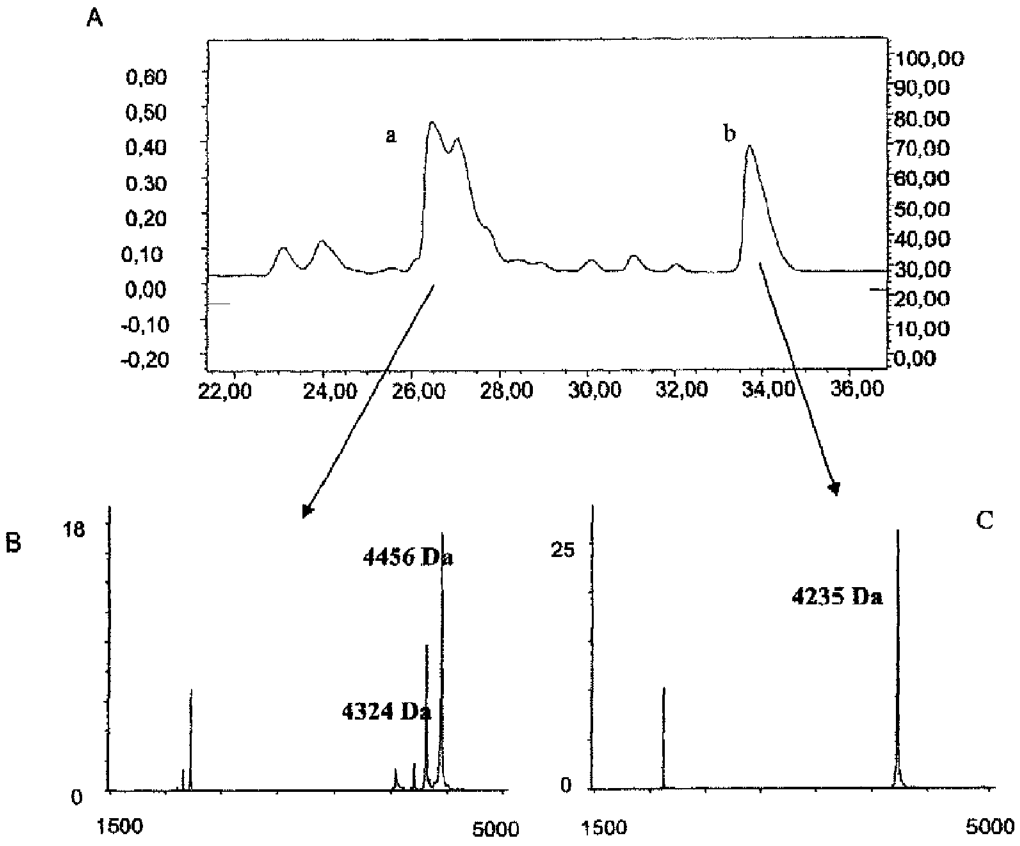
FIG. 4A: chromatogram obtained by reverse-phase HPLC of the active CM fraction; the y-axis, left-hand side, gives the absorption at 214 nm; the y-axis, right-hand side, gives the percentage of acetonitrile eluent; the x-axis gives the time in minutes
FIGS. 4B and 4C: mass spectrum of the fractions obtained from the reverse-phase HPLC; the x-axis gives the mass/charge; the y-axis gives the signal intensity

Activity was revealed in the two fractions designated as a (or "double peak") and b (or "single peak") (FIG. 4A). Analysis by mass spectrometry of these two fractions revealed the presence of three major peptides, the respective molecular masses of which are between 4230 and 4460 Da (FIGS. 4B and 4C).

The purification of RumC from cecal content was again performed using the three chromatographies developed, i.e. molecular screening, cation-exchange chromatography and reverse-phase chromatography. The elution profiles obtained are comparable to those of the first tests developed. The RumC purification method is thus reproducible and may therefore be adopted.

Figure 5:
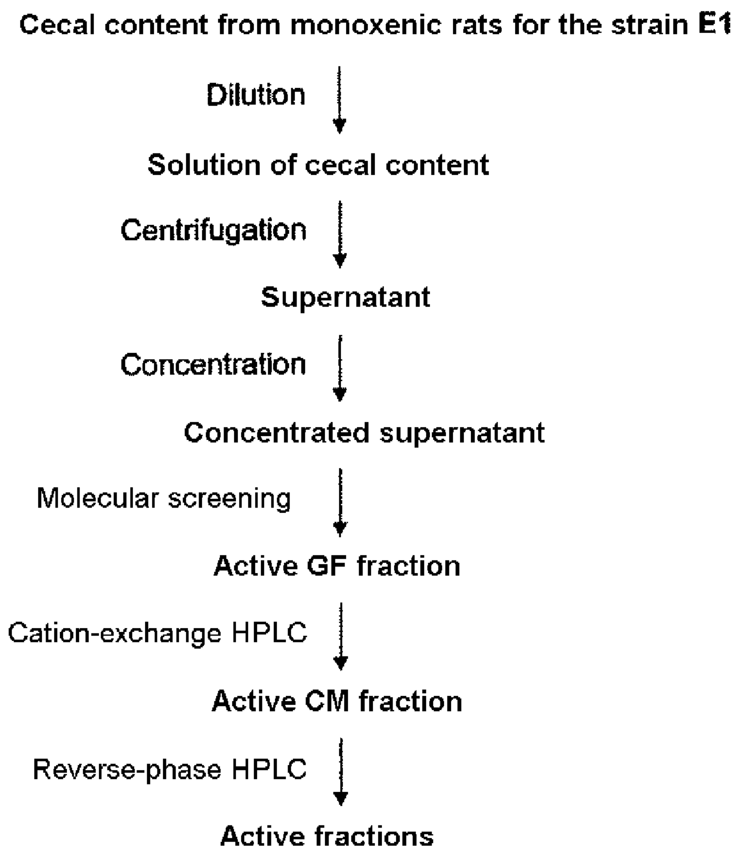
FIG. 5: scheme of the protocol for purifying RumC from the cecal content of monoxenic rats harboring the strain *R. gnavus* E1

The scheme summarizing the purification of RumC from cecal content is shown in FIG. 5.

1.9. Purification Yields and Factors

By Convention, the number of arbitrary activity units (AAU) present in a solution is defined as being the inverse of the last active dilution. A test of anti-*C. perfringens* activity was thus performed on serial dilutions (twofold) of each active fraction derived from the purification.

The purification factor is obtained by comparing the specific activities, expressed as AAU/mg of protein, of each fraction. An estimation of the amount of protein in the various fractions was deduced from the measurement of their absorption at 280 nm using a mass extinction coefficient $E^{0.1\%}$ of 1.8.

Table 4 gives the activity yields and the purification factors for the steps of the protocol for purifying RumC from the cecal content of monoxenic rats.

TABLE 4

Activity yields and purification factors during the preparation of RumC in vivo from 10 g of cecal content of monoxenic rats

| Fraction | V (mL) | anti-CpA A. (AAU) | $m_{protein}$ (mg) | SA (AAU/mg) | Yield | F purif. |
|---|---|---|---|---|---|---|
| Homogenate | 39 | 780 | nd | | 100% | |
| SN | 32 | 375 | 375 | 1 | 48% | 1 |
| Concentrated SN | 14 | 350 | 270 | 1.3 | 45% | 1.3 |
| Active GF | 66 | 205 | 20 | 10.3 | 26% | 10 |

TABLE 4-continued

Activity yields and purification factors during the preparation of RumC in vivo from 10 g of cecal content of monoxenic rats

| Fraction | V (mL) | anti-CpA A. (AAU) | $m_{protein}$ (mg) | SA (AAU/mg) | Yield | F purif. |
|---|---|---|---|---|---|---|
| Active CM | 1-1.5 | 170 | 0.135 | 1260 | 22% | 1200 |
| Double peak | 1-1.5 | 50 | nd | | 13% | |
| Single peak | 1-1.5 | 50 | nd | | | |

n.d. = not determined

V: total volume of the fraction in mL anti-CpA A.: anti-*C. perfringens* activity, i.e. the total number of activity units contained in the fraction $m_{protein}$: mass of protein in the fraction, expressed in mg SA: anti-*C. perfringens* specific activity in AAU/mg SA = anti-CpA A./$m_{protein}$ Yield: activity yield for the purification Yield = 100 × anti-CpA $A._{test\ fraction}$/anti-CpA $A._{homogenate}$ F purif.: purification factor F purif. = $SA_{test\ fraction}/SA_{SN}$ 1.10. Determination of the Peptide Sequence Although the molecular masses of the products present in the "double peak" and "single peak" fractions are different, Edman sequencing made it possible to establish a single major N-terminal sequence: AGXIXSGSVAV (SEQ ID No. 3).

In the two fractions concerned, a minor sequence of 17 residues was also revealed: AGPAYXVGYXGNNGAVT (SEQ ID No. 2).

2. Creation of a Mutant Strain by Random Mutagenesis

The technique adopted was random mutagenesis of the strain *R. gnavus* L14. This strain is a spontaneous mutant of *R. gnavus* E1 that has lost the capacity to produce RumA in vitro, but that still synthesizes RumC in vivo. This strain was exposed to a powerful alkylating agent, N-methyl-N'-nitro-N-nitrosoguanidine (NG).

Aliquot portions of the same culture of the strain L14 were thus exposed to increasing concentrations of NG (0 to 1000 μg/mL). After treatment, the various cell suspensions were diluted and then plated out on Petri dishes. Counting of the colonies after culturing made it possible to estimate the concentration of live cells in the various suspensions.

By comparison with the control concentration (tube 1, without NG treatment), a mortality rate could be determined for each treatment. It appears that the treatment with NG was effective: the mortality rates are between 50% and 99% and increase with the concentration.

In order to find the mutant(s) of interest, close to 860 colonies selected at random from the clones that survived the various treatments were subcultured on trypsin-supplemented agar medium and then subjected to an anti-*C. perfringens* activity test.

clones were found to be potential producers of an anti-*C. perfringens* substance on agar medium in the presence of trypsin.

Among these, 20 were selected for a more rigorous characterization.

In a first stage, the mutations affecting the clones were checked to make sure that they had not restored the chromosomal organization in rumA, via PCR.

The 20 selected clones were then subjected to anti-*Clostridium perfringens* activity tests on agar medium and in liquid medium, in the presence or absence of trypsin.

On trypsin-supplemented agar medium, an inhibition halo is present around seven of the twenty clones tested.

On the other hand, on trypsin-free agar medium, no clone produced any anti-*C. perfringens* substance: trypsin is thus always essential for the synthesis of the bacteriocin.

No anti-*C. perfringens* is produced by the clones cultured in liquid medium, even in the presence of trypsin.

3. Purification Using the Mutant Strain

Production and purification tests were performed on one of the seven productive clones, the mutant 9-17.

Figure 7:
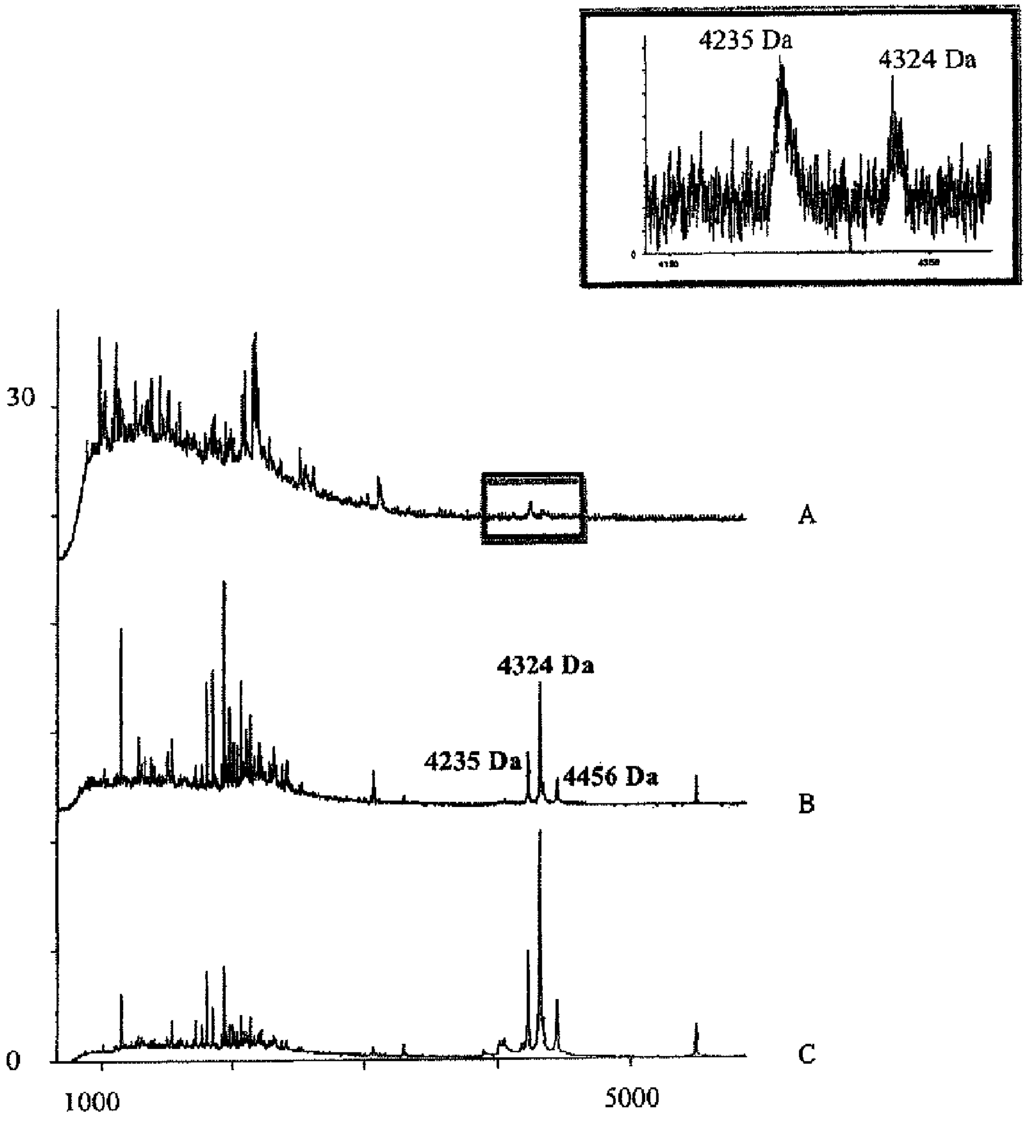
FIG. 7: mass spectra of the various fractions during the purification of RumC; the x-axis gives the mass/charge; the y-axis gives the signal intensity

The tests were performed on soft agar with variable concentrations of cells and of trypsin. After culturing the mutant, the agar was ground and then centrifuged to recover a supernatant (SN 9-17). This supernatant was then tested against *C. perfringens* and proved to be active. An analysis by mass spectrometry was performed on this active supernatant (FIG. 7A).

3.1. Chromatography on Cation-Exchange Resin Using the FPLC System

Before performing the ion-exchange chromatography, the sample needs to be desalted.

The first tests showed that desalting of SN 9-17 on Amicon was insufficient. Desalting of the sample on Sep-Pak should thus be envisioned as a preliminary purification step.

Elution of the proteins from the Sep-Pak is performed with a 40% acetonitrile solution. After evaporating off the acetonitrile on a rotavapor, the solution is equilibrated at pH 5 by diluting it in 20 mM, pH 5 sodium acetate buffer. From 65 mL of SN 9-17, 50 mL of desalted SN 9-17 equilibrated at pH 5 are obtained, and are loaded onto a carboxymethyl-Sepharose cation-exchange column.

Figure 6:
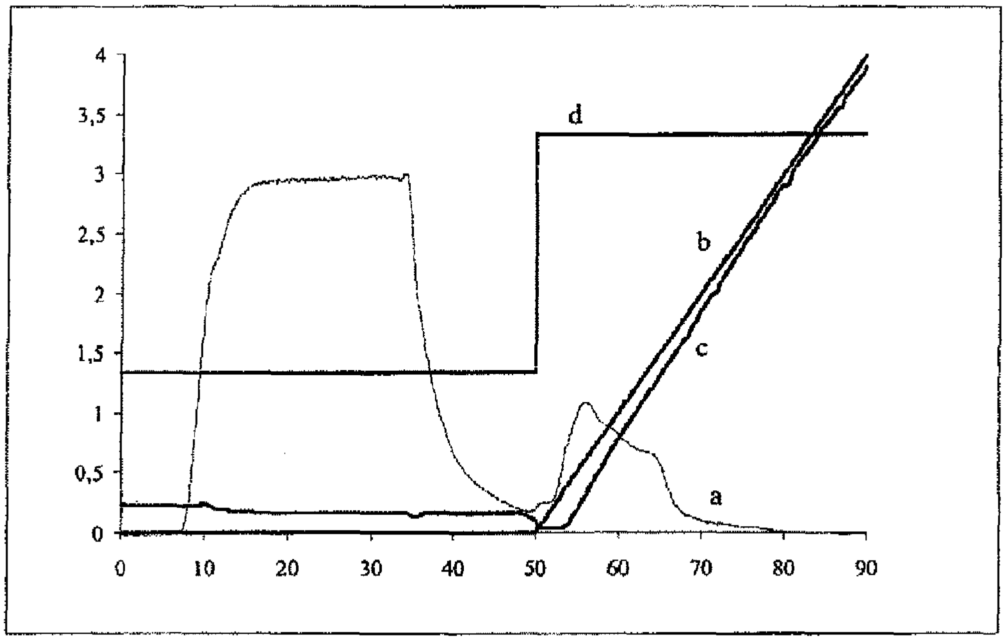
FIG. 6: chromatogram obtained by FPLC on a cation-exchange resin of the desalted fraction SN 9-17; the x-axis gives the time in minutes; the y-axis gives the absorption at 214 nm a: absorption at 214 nm b: NaCl concentration c: conductivity d: flow rate in mL/minute

The concentration gradient of 0 to 0.4 M NaCl was run for 40 minutes. The anti-*C. perfringens* activity is detected in the fractions eluted with 0.2 to 0.3 M NaCl, although very little protein material is present in these fractions when reference is made to the variation in absorption at 280 nm (FIG. 6). This had already been observed during the purification of RumC from cecal content. The active fractions were pooled and then desalted and concentrated on Sep-Pak. Analysis by mass spectrometry of this fraction ("active CM fraction") confirms the substantial gain in purification afforded by the cation-exchange chromatography and shows that the contaminants all have a molecular mass of less than 2500 Da (FIG. 7B).

3.2. Molecular Screening of the CM Fraction

Figure 8:
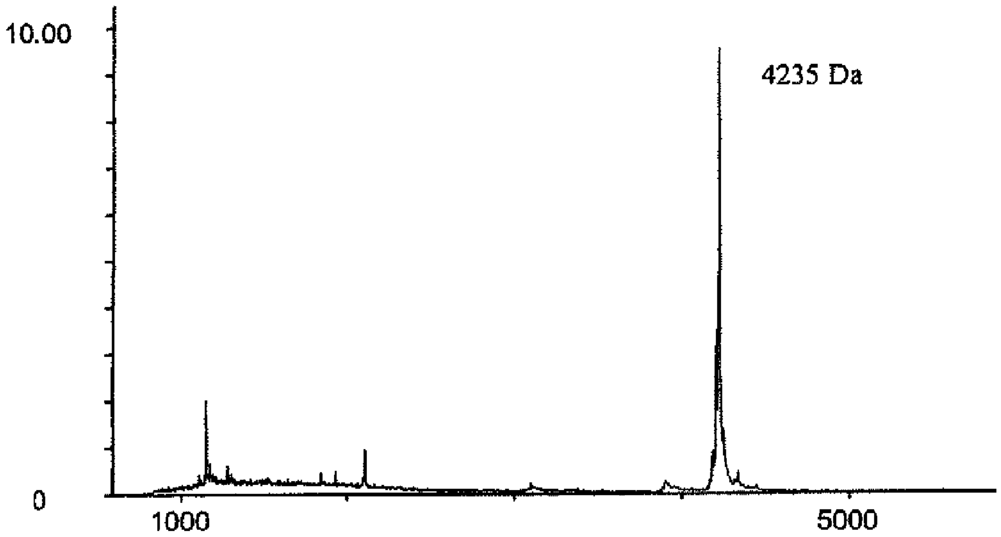
FIG. 8: mass spectrum of the fraction GF 47-50; the x-axis gives the mass/charge; the y-axis gives the signal intensity

Molecular screening of the active CM fraction was performed by means of the FPLC system on a column allowing the separation of peptides with a mass of less than 10 kDa. The elution is monitored by reading the variation in absorption at 280 nm; the amount of protein material is small and the separation proves to be unsatisfactory (not shown). The anti-*C. perfringens* activity was nonetheless tested in the collected fractions. Only 5% of the activity loaded is found after screening. This technique was therefore not adopted for the purification. On the other hand, the active fraction ("GF 47-50") was analyzed by mass spectrometry and proved to be virtually pure with a peptide of 4235 Da (FIG. 8).

3.3. Filtration of the CM Fraction

Another attempt to remove the contaminants from the active CM fraction was undertaken using filtration units. As RumC is retained by the 5 kDa filters (despite having a slightly lower molecular mass), a first test was performed with a Vivaspin 500 filtration unit whose cut-off threshold is 5 kDa. Unfortunately, the impurities are also retained by the filter, although their molecular masses are less than 2.5 kDa. Specifically, the mass spectrometry analysis does not reveal any gain in purification (results not shown). A second test was thus attempted with a Microcon filtration unit whose cut-off threshold is 10 kDa. Specifically, despite its molecular mass, it was previously observed that RumC could be retained by 10 kDa filters ("10 kDa R fraction"). The mass spectrometry analysis confirms the previous results and makes it possible to show that a large proportion of the contaminants is removed in the fraction not retained (FIG. 7C).

3.4. Reverse-Phase Chromatography on an HPLC System of the 10 kDa R Fraction

The 10 kDa R fraction containing the three RumC peaks (4235 Da, 4324 Da and 4456 Da) was then subjected to reverse-phase HPLC. The flow rate and gradient conditions are identical to those developed for the purification of RumC from cecal content, and the result obtained is comparable: two different fractions are active against *C. perfringens*, a "double-peak" fraction and a "single-peak" fraction.

3.5. Purification Yields and Factors

To evaluate the purification protocol, quantitative activity tests were performed using twofold serial dilutions of each active fraction. The number of arbitrary activity units (AAU) contained in each fraction was then calculated and the purification yield was deduced (Table 5). A substantial loss of active substance is observed during the steps of desalting of the culture supernatant, the cation-exchange chromatography followed by another desalting. It is quite likely that the loss takes place during the cation-exchange chromatography, but this does not place the validity of the protocol in doubt.

TABLE 5

Yields for the purification of RumC from the culture supernatant of the mutant 9-17

| Fraction | V (mL) | Anti-CpA A. (AAU) | Yield |
|---|---|---|---|
| SN 9-17 | 125 | 1453 | 100% |
| Active CM | ~3 | 300 | 21% |
| Double peak | 0.42 | 140 | } 19% |
| Single peak | 0.42 | 140 | |

V: total volume of the fraction in mL anti-CpA A. (anti-*C. perfringens* activity): total number of activity units contained in the fraction, in AAU Yield = 100 × anti-CpA $A._{test\ fraction}$/anti-CpA $A._{SN9\text{-}17}$; expressed in %

Another important criterion for evaluating a purification protocol is the demonstration of the gain in purification provided by each step. The purification factor is determined by comparing the specific activities (AAU/mg of protein) at each step, but to do this the mass of protein contained in each fraction must be measured. The purification monitoring was performed by mass spectrometry on account of the sensitivity of this method, making it possible to avoid "consuming" too much biological material. Although this method is not quantitative, the gain in purification was very clearly demonstrated.

3.6. Mass Spectrometry

The "double peak" and "single peak" fractions were analyzed by mass spectrometry. The results obtained are identical to those obtained with the fractions obtained from the purification using cecal content: the "double peak" fraction contains the 4324 Da and 4456 Da peptides, whereas the "single peak" fraction contains the 4235 Da peptide.

3.7. Sequencing

These fractions were thus sequenced.

For the "single peak" fraction, the sequence obtained is identical to the sequence already determined: AGXIXSGSVAV (SEQ ID No. 3). A minor sequence appears on the fifth cycle: AGPAY (SEQ ID No. 11).

As regards the "double peak" fraction, slight differences are noted: AGXVXSGSTAV (SEQ ID No. 12). The minor sequence is identical: AGPAY (SEQ ID No. 11).

Figure 9:
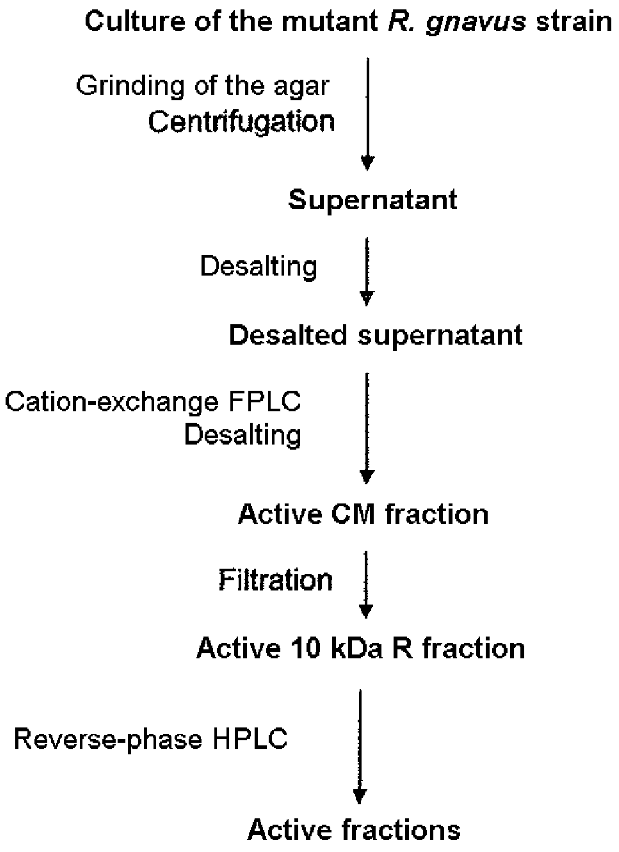
FIG. 9: scheme of the protocol for purifying RumC from the mutant strain LEM 9-17

The scheme summarizing the purification of RumC from the mutant strain is shown in FIG. 9.

The production of purified RumC is greatly simplified.

4. Characterization of the RumC Peptides 4.1. Antimicrobial Activity with Regard to Different Strains The antimicrobial activity of RumC was tested against different Gram+ and Gram− pathogenic strains, using in a first stage concentrated supernatant of the cecal content from monoxenic rats for the strain *R. gnavus* E1 (SN CCE1). Other tests were then performed with the two purified fractions against the strains sensitive to SN CCE1. The results are given in Table 6.

TABLE 6

Results of the tests of activity of RumC against different pathogenic strains

| | Strain tested | Antimicrobial activity (size of the inhibition halo) SN CCE1 | Fraction Double peak | Single peak |
|---|---|---|---|---|
| Gram+ | *Clostridium perfringens* CpA | + (2 mm) | + (1 mm) | + (1 mm) |
| | *Clostridium perfringens* S40 | + (2 mm) | + (1 mm) | + (1 mm) |
| | *Clostridium sporogenes* CIP 79-3 | — | nd | nd |
| | *Clostridium acetobutylicum* BL75-41 | — | nd | nd |
| | *Bacillus cereus* TZ 415 | + (2 mm) | + (5 mm) | + (3 mm) |
| | *Bacillus cereus* K 1231 | — | nd | nd |
| | *Bacillus cereus* Z 421 | — | nd | nd |
| | *Listeria monocytogenes* EGDE | + (1 mm) | + (1 mm) | + (1 mm) |
| | *Listeria monocytogenes* Scott A | — | nd | nd |
| | *Listeria inocula* CIP 80-12 | + (1 mm) | — | — |
| Gram− | *Salmonella enteridis* CIP 82-17 | + (5 mm) | — | — |
| | *Campylobacter jejuni* | — | nd | nd |

All the *Clostridium perfringens* strains tested are sensitive to the RumC peptide.

4.2. Antimicrobial Power Against *C. Perfringens*

The antimicrobial power of RumC was also evaluated by estimating the minimum inhibitory concentration of each purified RumC fraction "in vivo" and comparing it with that of metronidazole, a reference antibiotic used against *C. perfringens.*

To do this, twofold serial dilutions of the "double peak" and "single peak" fractions were prepared (up to the 1/512 dilutions). Tests of anti-*C. perfringens* activity were performed using these various dilutions and also metronidazole solutions at different concentrations (results not shown). From this test, the minimum inhibitory concentration of metronidazole is 25 μg/mL. This result is in agreement with the results previously obtained by Dabard et al. (Dabard et al., Appl. Environ. Microbiol., 67, 4111-4118, 2001).

As regards the "double peak" and "single peak" fractions, only the concentrated solutions (dilution 1) are active. Although the concentration of these solutions is not known with precision, it may be estimated, by virtue of the Edman sequencing, at about 40 μg/mL.

The antimicrobial power of RumC against *C. perfringens* thus appears to be comparable to that of metronidazole.

4.3. Resistance to Temperature

The first preliminary tests of resistance of RumC to heat were performed by incubating the same amount of peptide for 15 minutes at different temperatures. For the two "in vivo" RumC fractions ("double peak" and "single peak" fractions), a treatment of 15 minutes at 75° C. has no effect on the activity. However, at 100° C., the peptide is entirely inactivated within 15 minutes.

These tests were completed using samples of RumC purified from culture supernatant of the strain 9-17. The incubation time at the various temperatures was 5 minutes. The incubation time at 100° C. was 15 minutes.

The first temperature tested was 80° C. The first test was performed with the active CM fraction, the prepurified fraction containing the three peptides.

In contrast to the "double peak" and "single peak" fractions, the active CM fraction withstands a treatment of 15 minutes at 100° C.

The fraction GF 47-50 was then tested. This pure fraction containing only the 4235 Da peptide is sensitive to the 15-minute treatment at 100° C. It is also sensitive to a 5-minute treatment at 90° C. (Table 7).

TABLE 7

Summary table of the temperature resistance tests

| Incubation conditions: Temperature | Time | "in vivo" RumC: Double peak | Single peak | "in vitro" RumC: Active CM fraction | GF 47-50 |
|---|---|---|---|---|---|
| 50° C. | 15 min | R | R | / | / |
| 75° C. | 15 min | R | R | / | / |
| 80° C. | 5 min | / | / | R | / |
| 85° C. | 5 min | / | / | R | / |
| 90° C. | 5 min | / | / | R | S |
| 95° C. | 5 min | / | / | R | / |
| 100° C. | 15 min | s | s | R | s |

R = resistant;
s = sensitive;
/ = not tested 4.4. Resistance to pH

The resistance to pH of the peptides present in the active CM fraction was also tested at pH 2, pH 4.4 and pH 7.

The activity observed at pH 2 is comparable to that observed at pH 7. After incubation for 24 hours at 4° C., no loss of activity is observed at pH 2.

The peptides of the present invention are thus resistant to acidic pH and are especially suitable for use in animal nutrition or in the field of medicaments.

The invention claimed is:

1. An isolated peptide with antimicrobial activity, characterized in that it comprises a peptide chosen from the group consisting of SEQ ID No. 4, 5, and 6.

2. The isolated peptide as claimed in claim 1, wherein the peptide is isolated from a mutant strain of *Ruminococcus gnavus*.

3. The isolated peptide as claimed in claim 2, isolated from the strain of *Ruminococcus gnavus* deposited at the CNCM (Collection Nationale de Cultures de Microorganismes, Institut Pasteur, 25 rue du Docteur Roux, F-75015 Paris) on 19 Dec. 2006 under the number CNCM I-3705.

4. A polynucleotide coding for an isolated peptide as claimed in claim 1, wherein the polynucleotide is a cDNA.

5. An expression cassette, characterized in that it comprises, in the transcription direction:

a promoter that is functional in a host organism, a polynucleotide as claimed in claim 4, and a terminator sequence in the same host organism.

6. A vector comprising a polynucleotide as claimed in claim 4.

7. A host organism transformed with a polynucleotide as claimed in claim 4.

8. The strain of *Ruminococcus gnavus* deposited at the CNCM (Collection Nationale de Cultures de Microorganismes, Institut Pasteur, 25 rue du Docteur Roux, F-75015 Paris) on 19 Dec. 2006 under the number CNCM I-3705.

9. A protein mixture or fermentation must that is obtained from the host organism as claimed in claim 7.

10. A composition comprising an isolated peptide as claimed in claim 1.

11. The composition as claimed in claim 10, which is in liquid form or in powder form.

12. A nutritional additive comprising an isolated peptide as claimed claim 1.

13. The nutritional additive as claimed in claim 12, which is in liquid form or in powder form.

14. An animal feed, characterized in that it comprises a nutritional base for animals and a nutritional additive as claimed in claim 12.

15. A method of preparing a medicament or a nutritional additive or an animal feed comprising the step of incorporating an isolated peptide as claimed in claim 1 into the medicament, the nutritional additive, or the animal feed.

16. The method of claim 15, wherein the medicament or the nutritional additive is for preventing or treating necrotic enteritis caused by *C. perfingens* in pigs or poultry.

17. The method of claim 15, wherein medicament or the nutritional additive is for preventing or treating gastrointestinal diseases in man caused by *C. perfingens*.

18. A method of nontherapeutic treatment of animals comprising the step of administering the isolated peptide of claim 1 to the animals.

* * * * *

SEQUENCE LISTING

```
<160> NUMBER OF SEQ ID NOS: 12

<210> SEQ ID NO 1
<211> LENGTH: 17
<212> TYPE: PRT
<213> ORGANISM: Ruminococcus gnavus
<220> FEATURE:
```

-continued

<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 1

Ala Gly Pro Ala Tyr Xaa Val Gly Tyr Xaa Gly Asn Xaa Gly Xaa Val
1 5 10 15

Thr

<210> SEQ ID NO 2
<211> LENGTH: 17
<212> TYPE: PRT
<213> ORGANISM: Ruminococcus gnavus
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 2

Ala Gly Pro Ala Tyr Xaa Val Gly Tyr Xaa Gly Asn Asn Gly Ala Val
1 5 10 15

Thr

<210> SEQ ID NO 3
<211> LENGTH: 11
<212> TYPE: PRT
<213> ORGANISM: Ruminococcus gnavus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 3

Ala Gly Xaa Ile Xaa Ser Gly Ser Val Ala Val
1 5 10

<210> SEQ ID NO 4
<211> LENGTH: 63
<212> TYPE: PRT
<213> ORGANISM: Ruminococcus gnavus

<400> SEQUENCE: 4

Met Arg Lys Ile Val Ala Gly Lys Leu Gln Thr Gly Ala Asp Phe Glu
1 5 10 15

Gly Ser Lys Trp Gly Cys Val Cys Ser Gly Ser Thr Ala Val Ala Asn
20 25 30

Ser His Asn Ala Gly Pro Ala Tyr Cys Val Gly Tyr Cys Gly Asn Asn
35 40 45

-continued

```
Gly Val Val Thr Arg Asn Ala Asn Ala Asn Val Ala Lys Thr Ala
    50                  55                  60


<210> SEQ ID NO 5
<211> LENGTH: 63
<212> TYPE: PRT
<213> ORGANISM: Ruminococcus gnavus

<400> SEQUENCE: 5

Met Arg Lys Ile Val Ala Gly Lys Leu Gln Thr Gly Ala Asp Phe Glu
1               5                   10                  15

Gly Ser Lys Gly Gly Cys Lys Cys Ser Gly Gly Ala Val Val Glu Asn
            20                  25                  30

Ser His Asn Ala Gly Pro Ala Tyr Cys Val Gly Tyr Cys Gly Asn Asn
        35                  40                  45

Gly Val Val Thr Arg Asn Ala Asn Ala Asn Leu Ala Arg Thr Lys
    50                  55                  60


<210> SEQ ID NO 6
<211> LENGTH: 63
<212> TYPE: PRT
<213> ORGANISM: Ruminococcus gnavus

<400> SEQUENCE: 6

Met Lys Leu Val Glu Thr Lys Thr Thr Lys Thr Gly Thr Asn Phe Glu
1               5                   10                  15

Gly Asn Arg Ala Gly Cys Ile Cys Asn Gly Thr Val Ala Val Ala Asn
            20                  25                  30

Ser His Asn Ala Gly Pro Ala Tyr Cys Val Gly Tyr Cys Gly Asn Ser
        35                  40                  45

Gly Val Val Thr Arg Asn Ala Asn Ala Asn Val Ala Lys Thr Ala
    50                  55                  60


<210> SEQ ID NO 7
<211> LENGTH: 192
<212> TYPE: DNA
<213> ORGANISM: Ruminococcus gnavus

<400> SEQUENCE: 7

atgagaaaaa tcgtagcagg aaagttacag acaggagcag actttgaagg cagcaaatgg      60

ggatgtgttt gtagtggaag cacagcagta gcaaactctc ataatgcagg accggcgtat     120

tgcgtaggat actgtggaaa caacggagta gtgactagaa atgctaatgc aaatgtcgca     180

aaaacggcat aa                                                         192


<210> SEQ ID NO 8
<211> LENGTH: 192
<212> TYPE: DNA
<213> ORGANISM: Ruminococcus gnavus

<400> SEQUENCE: 8

atgagaaaaa tcgtagcagg aaagttacag acaggagcag actttgaagg cagcaaaggt      60

ggatgtaaat gcagtggcgg tgcagtagta gaaaactctc ataatgcagg accagcgtat     120

tgcgtgggat actgtggaaa caacggagtg gtaacaagaa atgcgaatgc gaatcttgca     180

agaacaaaat aa                                                         192


<210> SEQ ID NO 9
<211> LENGTH: 192
<212> TYPE: DNA
<213> ORGANISM: Ruminococcus gnavus
```

-continued

```
<400> SEQUENCE: 9

atgaaattag tagaaacaaa aacaacaaaa acaggaacaa actttgaagg gaatagagct     60

ggatgtattt gtaatggcac tgtagcagta gcaaattctc ataatgcagg accagcatat    120

tgtgttgggt attgcggaaa tagtggagta gtaacaagaa atgcgaatgc aaatgtcgca    180

aaaacagcat aa                                                        192


<210> SEQ ID NO 10
<211> LENGTH: 11
<212> TYPE: PRT
<213> ORGANISM: Ruminococcus gnavus
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be Asn or Ser
<220> FEATURE:
<221> NAME/KEY: misc_feature
<222> LOCATION: (9)..(9)
<223> OTHER INFORMATION: Xaa can be any naturally occurring amino acid

<400> SEQUENCE: 10

Ala Gly Val Ile Xaa Xaa Gly Thr Xaa Ala Val
1               5                   10


<210> SEQ ID NO 11
<211> LENGTH: 5
<212> TYPE: PRT
<213> ORGANISM: Ruminococcus gnavus

<400> SEQUENCE: 11

Ala Gly Pro Ala Tyr
1               5


<210> SEQ ID NO 12
<211> LENGTH: 11
<212> TYPE: PRT
<213> ORGANISM: Ruminococcus gnavus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 12

Ala Gly Xaa Val Xaa Ser Gly Ser Thr Ala Val
1               5                   10
```